(12) United States Patent
Sevrain (10) Patent No.: US 8,696,713 B2
(45) Date of Patent: Apr. 15, 2014

(54) ANCHORING DEVICE FOR POSTERIORLY ATTACHING ADJACENT VERTERBRAE

(75) Inventor: Lionel C. Sevrain, West Palm Beach, FL (US)

(73) Assignee: Lers Surgical, LLC, West Palm Beach, FL (US)

( * ) Notice: Subject to any disclaimer, the term of this patent is extended or adjusted under 35 U.S.C. 154(b) by 807 days.

(21) Appl. No.: 12/520,574

(22) PCT Filed: Dec. 26, 2007

(86) PCT No.: PCT/US2007/088810
§ 371 (c)(1),
(2), (4) Date: Jan. 27, 2010

(87) PCT Pub. No.: WO2008/080164
PCT Pub. Date: Jul. 3, 2008

(65) Prior Publication Data
US 2010/0160970 A1  Jun. 24, 2010

Related U.S. Application Data

(60) Provisional application No. 60/876,466, filed on Dec. 22, 2006.

(51) Int. Cl.
*A61B 17/70* (2006.01)
(52) U.S. Cl.
USPC .................. 606/277; 285/412; 269/249
(58) Field of Classification Search
USPC .................. 606/247, 277, 278; 269/203, 249; 285/412
See application file for complete search history.

(56) References Cited

U.S. PATENT DOCUMENTS

| | | | | |
|---|---|---|---|---|
| 1,559,866 A | * | 11/1925 | Greathead et al. | 269/248 |
| 2,121,085 A | * | 6/1938 | Krumholz | 269/249 |
| 2,190,585 A | * | 2/1940 | Rhinevault | 269/249 |
| 2,515,308 A | * | 7/1950 | Birger | 29/446 |
| 2,549,429 A | * | 4/1951 | Cowles | 29/257 |
| 2,576,904 A | * | 11/1951 | Jessen et al. | 269/203 |
| 3,359,534 A | * | 12/1967 | Lewis et al. | 439/758 |
| 5,531,746 A | | 7/1996 | Errico et al. | 606/61 |
| 5,645,599 A | * | 7/1997 | Samani | 623/17.16 |
| D390,954 S | | 2/1998 | Kumar et al. | D24/143 |
| 5,928,233 A | | 7/1999 | Apfelbaum et al. | 606/61 |
| 6,187,005 B1 | * | 2/2001 | Brace et al. | 606/264 |
| 6,328,738 B1 | | 12/2001 | Suddaby | 606/57 |
| 6,547,790 B2 | | 4/2003 | Harkey, III et al. | 606/61 |
| 6,712,825 B2 | * | 3/2004 | Aebi et al. | 606/90 |

(Continued)

OTHER PUBLICATIONS

Ebraheim, "Posterior lateral mass screw fixation: anatomic and radiographic considerations," *The University of Pennsylvania Orthopaedic Journal*, 12:66-72, 1999.

(Continued)

*Primary Examiner* — Ellen C Hammond
*Assistant Examiner* — Stuart S Bray
(74) *Attorney, Agent, or Firm* — Novak Druce Connolly Bove + Quigg LLP (57) ABSTRACT

An anchoring device for attaching an upper vertebra adjacent to a lower vertebra comprises a clamp having a first end and a second end opposite the first end, adapted to be positioned around upper and lower lateral masses of the adjacent vertebrae, and a fastener which in an installed position engages opposite ends of the clamp and which engages adjacent vertebrae thereby attaching the adjacent vertebrae together.

10 Claims, 5 Drawing Sheets

(56) References Cited

U.S. PATENT DOCUMENTS

| | | | |
|---|---|---|---|
| 6,786,907 B2* | 9/2004 | Lange | 606/250 |
| 6,805,716 B2* | 10/2004 | Ralph et al. | 623/17.16 |
| 7,008,426 B2 | 3/2006 | Paul | 606/70 |
| 7,104,896 B2* | 9/2006 | Wood | 473/98 |
| 7,591,837 B2* | 9/2009 | Goldsmith | 606/247 |
| 7,722,645 B2* | 5/2010 | Bryan | 606/246 |
| 7,799,057 B2* | 9/2010 | Hudgins et al. | 606/247 |
| 7,871,426 B2* | 1/2011 | Chin et al. | 606/248 |
| 7,935,136 B2* | 5/2011 | Alamin et al. | 606/279 |
| 8,002,801 B2* | 8/2011 | Carl et al. | 606/246 |
| 2003/0199874 A1* | 10/2003 | Michelson | 606/61 |
| 2004/0049191 A1 | 3/2004 | Markworth et al. | 606/61 |
| 2004/0092929 A1* | 5/2004 | Zindrick | 606/61 |
| 2004/0143270 A1* | 7/2004 | Zucherman et al. | 606/79 |
| 2005/0119657 A1* | 6/2005 | Goldsmith | 606/61 |
| 2005/0267579 A1* | 12/2005 | Reiley et al. | 623/17.11 |
| 2006/0036243 A1* | 2/2006 | Sasso et al. | 606/61 |
| 2006/0036246 A1* | 2/2006 | Carl et al. | 606/61 |
| 2006/0058790 A1* | 3/2006 | Carl et al. | 606/61 |
| 2006/0224159 A1* | 10/2006 | Anderson | 606/61 |
| 2006/0241601 A1* | 10/2006 | Trautwein et al. | 606/61 |
| 2006/0265069 A1* | 11/2006 | Goble et al. | 623/17.11 |
| 2008/0177326 A1* | 7/2008 | Thompson | 606/277 |
| 2008/0183209 A1* | 7/2008 | Robinson et al. | 606/246 |
| 2008/0294199 A1* | 11/2008 | Kohm et al. | 606/248 |
| 2008/0294200 A1* | 11/2008 | Kohm et al. | 606/279 |

OTHER PUBLICATIONS

PCT International Search Report issued in International Application No. PCT/US2007/088810, mailed Jun. 26, 2008.

Vender et al., "The Evolution of Posterior Cervical and Occipitocervical Fusion: Atlantoaxial Fusion," Medscape, 2004.

* cited by examiner

FIG. 4 POSTERIOR

FIG. 5 SIDE

FIG. 6 TOP

ANCHORING DEVICE FOR POSTERIORLY ATTACHING ADJACENT VERTERBRAE

RELATED APPLICATION

This Application is a National Phase Application of International Application No. PCT/US2007/088810 filed Dec. 12, 2007, which claims priority to U.S. Provisional Patent Application No. 60/876,466, filed Dec. 22, 2006.

FIELD OF THE INVENTION

The present invention relates to the devices for fusing adjacent vertebrae of the spinal column and, more particularly, to a posterior fixation device for attaching at least two adjacent cervical vertebrae together.

BACKGROUND OF THE INVENTION

Posterior cervical fixation using lateral mass plates has been shown to be a safe and effective method to achieve cervical fusion of adjacent vertebrae. In this technique, a plate is secured posteriorly on two superposed lateral mass plates of adjacent vertebrae typically with a pair of screws each engaging respective lateral mass plates of the two vertebrae, thereby fusing the two vertebrae together. Lateral mass plating is biomechanically superior to laminar wiring or clamping in limiting cervical motion. In addition, unlike posterior laminar wiring or clamping, lateral mass plating does not require the presence of the posterior elements (lamina, spinous process). During the last ten years, posterior plating using lateral mass screw fixation has become more popular for treating instability of the lower cervical spine. Injury to the spinal nerves associated with insertion of lateral mass screws is a complication of this procedure.

Several techniques for lateral screw placement have been developed. Each has its unique entrance point for screw insertion and screw trajectory. Rods connect screws inserted into adjacent vertebrae together. More than one screw (and corresponding multiple vertebrae) may be connected to one rod. Other known techniques for fusing vertebrae include the so-called Mageri technique, the Anderson technique, the An Technique, etc. All of these known techniques involve inserting a screw into a single vertebra.

Known vertebrae connection devices have some drawbacks. They are difficult to contour, and the screw positions are dictated by the fixed plate entry holes. In addition, the screw trajectories are divergent from the plate entry holes, and the connection of the screw to the plate is not rigid. Also, there is no space to pack autograft bone under a screw-plate connection. Screws placed medially or laterally cannot be captured by the plate. Successive screws cannot be compressed or distracted because of the fixed plate hole distances. Moreover, if the plate needs to be revised, the screws must be removed. There is therefore a need for an improved posterior cervical anchoring device.

SUMMARY OF THE INVENTION

In accordance with a first aspect, an anchoring device for attaching an upper vertebra adjacent to a lower vertebra comprises a clamp having a first end and a second end opposite the first end, adapted to be positioned around upper and lower lateral masses of the adjacent vertebrae, and a fastener which in an installed position engages opposite ends of the clamp and which engages adjacent vertebrae thereby attaching the adjacent vertebrae together.

From the foregoing disclosure and the following more detailed description of various preferred embodiments it will be apparent to those skilled in the art that the present invention provides a significant advance in the technology of vertebrae fusion. Particularly significant in this regard is the potential the invention affords for providing a high quality, low cost anchoring device for attaching adjacent vertebrae together. Additional features and advantages of various preferred embodiments will be better understood in view of the detailed description provided below.

It should be understood that the appended drawings are not necessarily to scale, presenting a somewhat simplified representation of various preferred features illustrative of the basic principles of the invention. The specific design features of the vertebrae fusion device as disclosed here, including, for example, the specific dimensions of the clamp, will be determined in part by the particular intended application and use environment. Certain features of the illustrated embodiments have been enlarged or distorted relative to others to improve visualization and clear understanding. In particular, thin features may be thickened, for example, for clarity of illustration. All references to direction and position, unless otherwise indicated, refer to the orientation illustrated in the drawings.

DETAILED DESCRIPTION OF CERTAIN PREFERRED EMBODIMENTS

It will be apparent to those skilled in the art, that is, to those who have knowledge or experience in this area of technology that many uses and design variations are possible for the vertebrae fusion device disclosed here. The following detailed discussion of various alternative and preferred features and embodiments will illustrate the general principles of the invention with reference to vertebrae fusion device suitable for use attaching adjacent vertebrae together at the lateral masses. Other embodiments suitable for other applications such will be apparent to those skilled in the art given the benefit of this disclosure.

Figure 1:
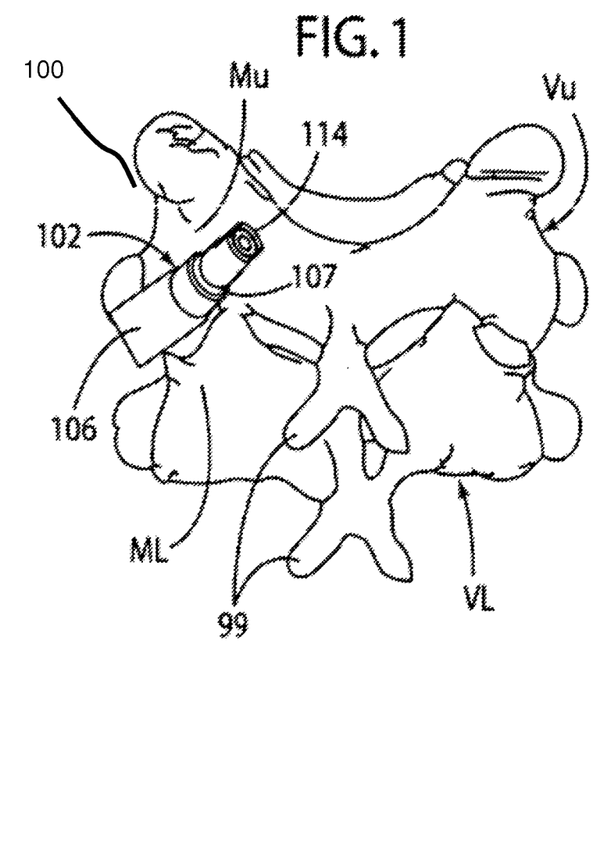
FIG. 1 is a schematic slightly superior posterior view of an anchoring device in accordance with a preferred embodiment, showing a clamp and a screw attached to adjacent vertebrae.

Referring now to the drawings, FIG. 1 shows a slightly superior posterior view of an anchoring device 100 in accordance with a preferred embodiment, showing a clamp 102 and a screw 104 attached to adjacent vertebrae. As understood herein, the length of the spinal column is considered to be generally in an upward/downward direction or Z-axis, with an upper vertebra $V_U$ shown above a lower vertebra $V_L$ in FIG. 1. Each vertebra has a spinous process 99 positioned generally in the center of the vertebrae and on a posterior side. Left and right of the spinous process is an X-axis. The side of the vertebrae opposite the posterior side is the anterior side. Thus, posterior/anterior refers to a Y-axis in and out of the plane of the paper in FIG. 1, and left-right in the side view of FIG. 2. Each vertebra comprises lateral masses M. The lateral mass of the lower vertebra $V_L$ is identified as $M_L$, the lateral mass of the upper vertebra $V_U$ is identified as $M_U$. The articulation between the lower articular facet of the lateral mass $M_U$ of the upper vertebra $V_U$ and the upper articular facet of the lateral mass $M_L$ of the lower vertebra $V_L$, is identified as X.

Figure 2:
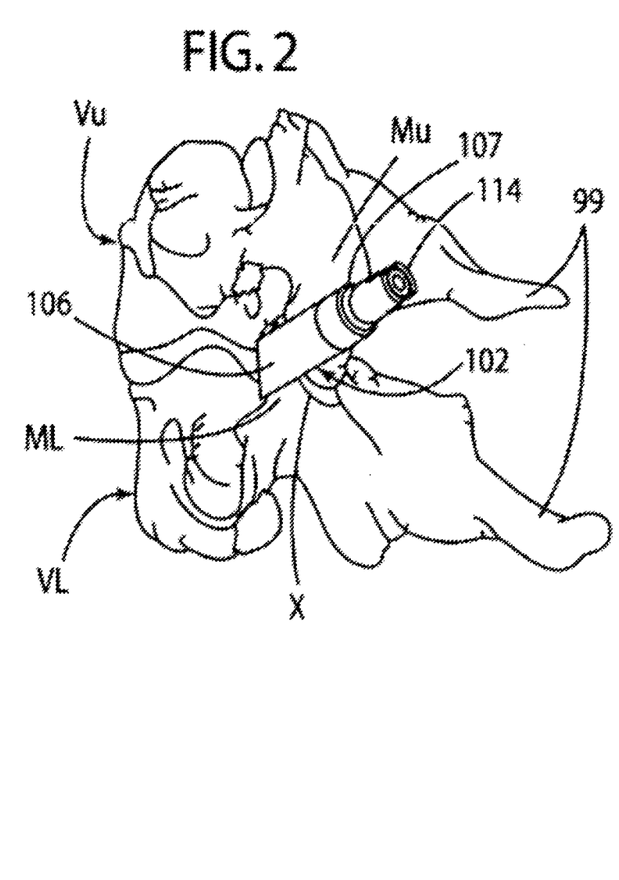
FIG. 2 is a side view of the anchoring device of FIG. 1.
Figure 3:
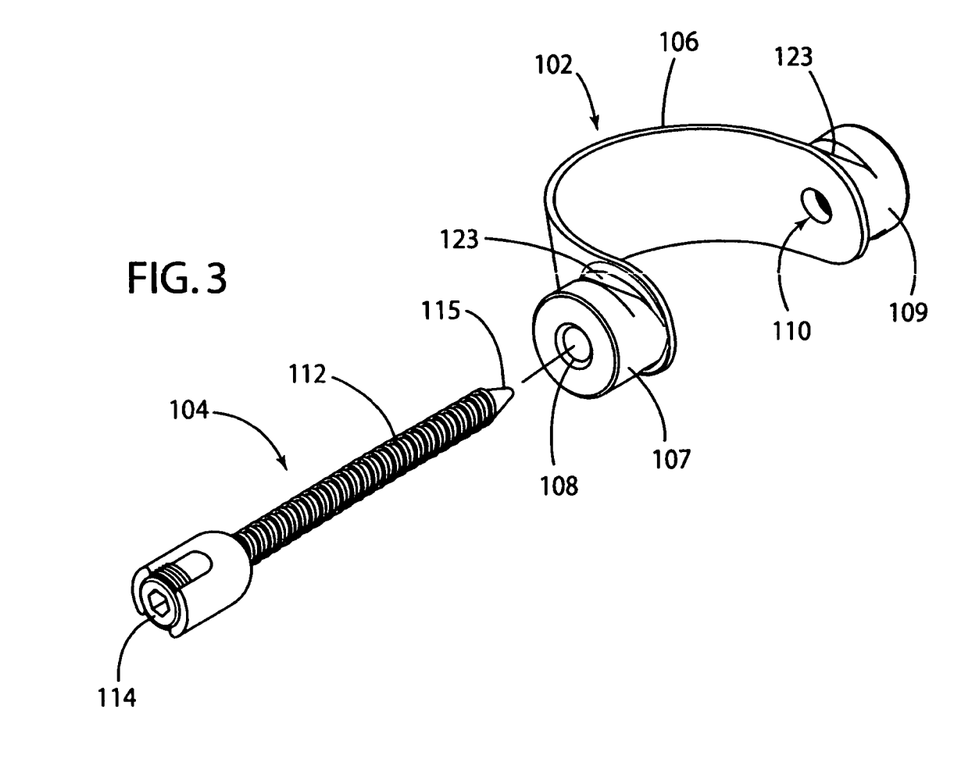
FIG. 3 is an isolated exploded perspective view of the anchoring device in accordance with a preferred embodiment.

In accordance with a highly advantageous feature, the anchoring device 100 joins a pair of adjacent vertebrae. The clamp 102 is positioned around upper and lower lateral masses $M_U$, $M_L$ of adjacent vertebrae, and the fastener 104 engages the clamp and engages bone from both lateral masses, along a trans-articular pathway, thereby attaching the vertebrae together. That is, the fastener is engaged into an inferior articular process of the upper vertebra, then pierces the articular surface of the facet, then extends through an inter-vertebral joint (i.e., is trans-articular), then pierces the cortex of the articular facet of the superior articular process of the lower vertebra, and then stops before breaking the anterior cortex of the intervertebral foramen to avoid injury to neurovacular elements. FIGS. 1-2 show the clamp and screw in an installed position, connecting a pair of vertebrae. As best seen in FIG. 3, the clamp 102 has a body 106 that has generally a "C" shape such that it can be positioned around the lateral masses M of two superposed cervical vertebrae. The clamp 102 also defines a pair of openings at its opposed ends, that is a proximal posterior opening 108 at a first end 107 and a distal anterior opening 110 at second end 109. Both the openings 108 and 110 are adapted to receive a stem 112 of the screw 104. The openings may each independently be threaded or unthreaded. In some cases, the openings 108 and 110 may be adapted to be tapped by the screw 104 as it rotatably introduced through the clamp 102. In other cases, both the openings 108 and 110 may define female threads adapted to be threadably engaged by the screw 104 (as in a nut and bolt arrangement) as it rotatably introduced through the clamp 102. As shown here, the screw is a polyaxial screw 104 having a screw head 114 and screw end 115. Grooves 123 may be formed in the clamp to receive an installation tool, discussed in greater detail below.

The posterior opening 108 is preferably the first opening that receives the screw 104. In one preferred embodiment the posterior opening can be dimensioned so that the screw 104 can slide therethrough (i.e. without tapping any threads in the clamp 102), with the anterior or distal opening 110 being either tapped by the screw 104 or threadably engaged thereby if the anterior opening 110 already defines female threads therein. In this same alternative, the anterior or distal opening 110 can take the form of a "blind" hole, that is a recessed hole or pocket which typically defines female threads that are adapted to threadably engage the free distal end of the screw 104. This arrangement is particularly advantageous in that the screw 104 cannot extend past the clamp 102, thereby preventing the screw 104 from possibly contacting adjacent vasculonervous elements, such as the spinal nerves and vertebral artery. Accordingly, even though the opening 110 is herein illustrated as a through-opening, it can conveniently be at least partly blocked by a bottom wall located on the anterior side of the clamp 102, for again preventing the screw 104 from extending past the clamp 102. When the screw 104 is inserted, it threadably engages the recessed opening 110 until it abuts the aforementioned bottom wall.

When the distal opening 110 of the clamp 102 is a through-hole, the length of the screw 104 may be chosen or adjusted so that the screw 104 does not extend past the opening 110, once the screw 104 has been fully inserted in the clamp 102 and in the bone of the lateral masses $M_U$ and $M_L$. Preferably, the screw 104 extends from the posterior opening 108 to the anterior opening 110 of the clamp 102 while threadably engaging the bone of the superposed lateral masses $M_U$ and $M_L$ of the upper and lower vertebrae $V_U$ and $V_L$, thereby connecting the two lateral masses $M_U$ and $M_L$ together in an inter-articular connection of the adjacent vertebrae $V_U$ and $V_L$. The screw 104 thus threadably engages at its distal/anterior end 115 the anterior opening 110 of the clamp 102 and holds the posterior end of the clamp 102 via its screw head 114, whereby the clamp 102 is in compression around the lateral masses $M_U$ and $M_L$ and securely holds the upper and lower vertebrae $V_U$ and $V_L$ together.

Figure 8:
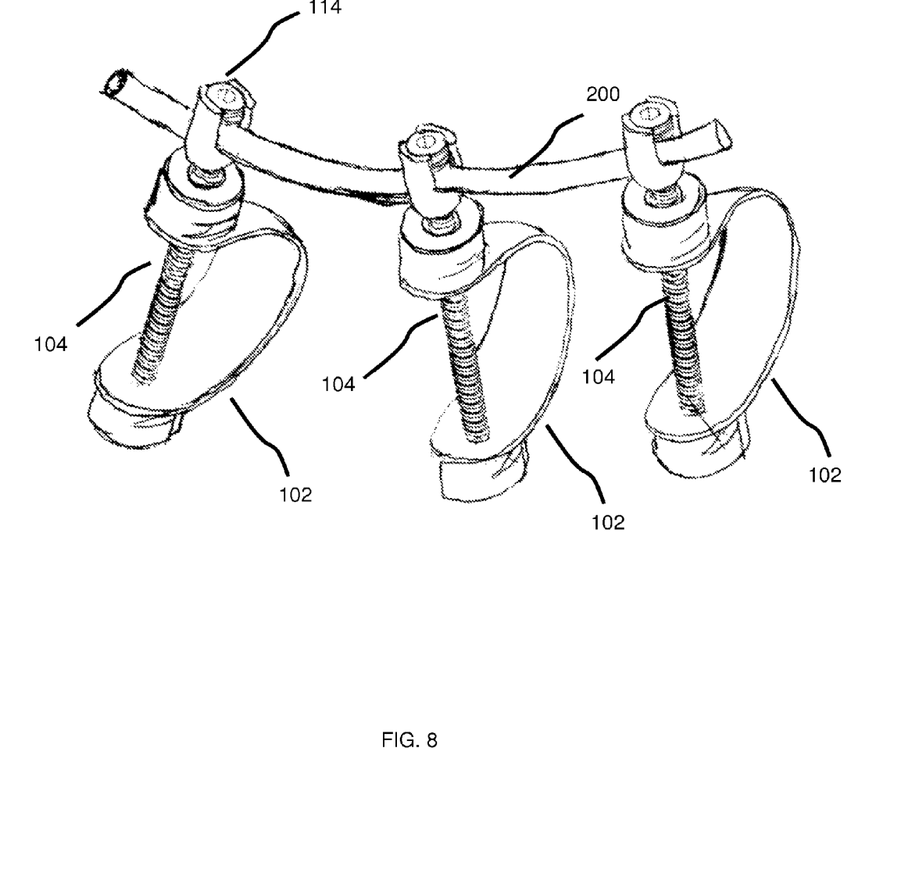
FIG. 8 is a schematic illustration of a plurality of claims attached to an osteosynthesis rod.

The screw 104 can be a telescopic screw or have different types of rotatably independent threads (for instance, a screw of the type disclosed in International Patent Publication WO 2005/107619 to Sevrain), and its threaded stem 112 is adapted to tap the bone of the lateral masses $M_U$ and $M_L$ so as to anchor itself therein. Other types of screws suitable for use here will be readily apparent to those skilled in the art given the benefit of this disclosure. The head 114 of the screw 104 preferably is polyaxial as shown in FIG. 3 so as to allow its orientation to be adjusted with respect to the screw. This is advantageous where an osteosynthesis rod 200 is used which secure together a plurality of screws and therefore a plurality of vertebrae, as illustrated in FIG. 8.

Figure 4:
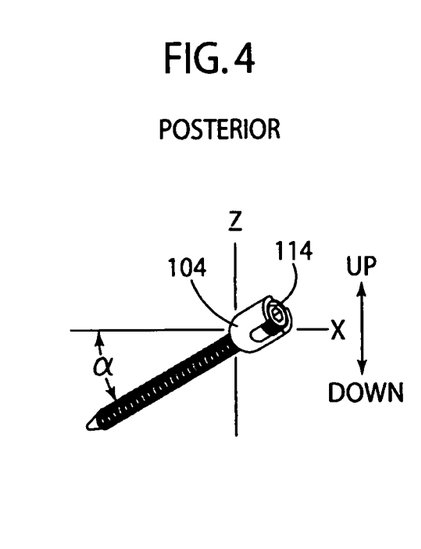
FIG. 4 is a schematic posterior side view of the screw shown in an installed position with vertebrae removed for clarity of illustration.
Figure 5:
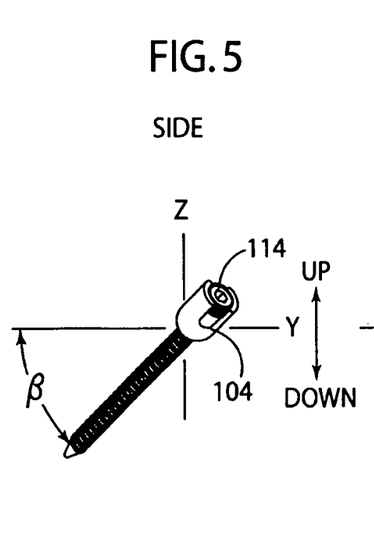
FIG. 5 is a schematic side view of the clamp and screw shown in an installed position with vertebrae removed for clarity of illustration.
Figure 6:
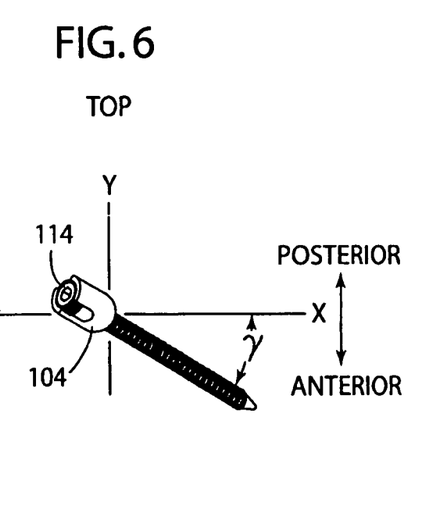
FIG. 6 is a schematic top side view of the screw shown in an installed position with vertebrae removed for clarity of illustration.

The clamp 102 is destined to be brought to the lateral masses $M_U$ and $M_L$ via a posterior approach, with the screw 104 being adapted to threadably engage in a trans-articular manner the lateral masses $M_U$ and $M_L$ (through the articular facets thereof) thereby connecting the two ends of the clamp 102 together. FIGS. 4-6 show installed positions of the fastener taken from one of a posterior side (FIG. 4), side view (FIG. 5) and top side view (FIG. 6). In FIGS. 4 and 5, the up direction is upward in the plane of the paper. In FIG. 6, upward in the plane of the paper is the posterior side. In each case, the fastener makes an acute angle with the horizontal. Thus, the screw 104 extends through the inferior articular process of the upper vertebra $V_U$ and through the superior articular process of the lower vertebra $V_L$, along an oblique direction that is downwardly, outwardly (away from the spinous process) and forwardly (from the posterior side towards the anterior side) oriented as those terms are used herein.

The shape of the clamp 102 can be customized in view of the different anatomical configurations of the superposed lateral masses $M_L$ and $M_U$ (including the articular facets thereof). The clamp 102 can be made of a plastics material, resin, etc., which can be custom-constructed using computer-controlled milling machines, which have been previously programmed with the details of shape and configuration of the lateral masses. The clamp 102 can also be molded.

Figure 7:
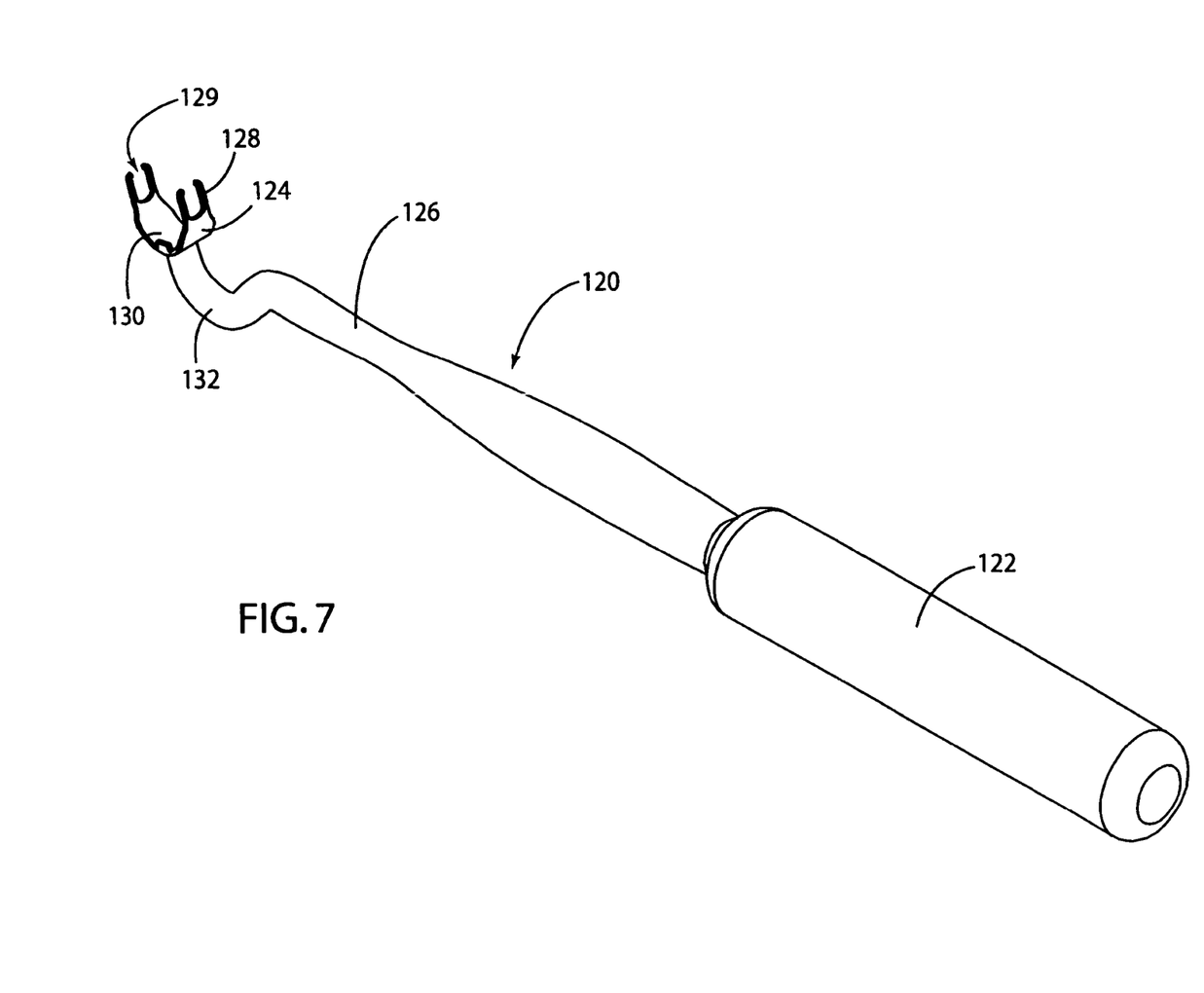
FIG. 7 is perspective view of an installation tool in accordance with a preferred embodiment used to hold the clamp in an installed position while the fastener is attached to the clamp and to the vertebrae.

In accordance with another highly advantageous feature, there is provided an installation tool 120 for use with the above implant 100, wherein the installation tool has a handle and a clamp-holding head adapted to bring the clamp around the upper and lower lateral masses of the adjacent vertebrae and adapted to retain the clamp in the installed position until the clamp has been secured to the lateral masses by way of the threaded fastener. FIG. 7 shows a perspective view of a preferred embodiment of an installation tool 120 that comprises a handle 122, a distal holding head or fork 124, and a stem 126 therebetween. The holding fork 124 is adapted to carry the clamp 102 to the lateral masses $M_U$ and $M_L$, as seen in FIGS. 1 and 2. For instance, the clamp 104 can be set into the holding fork 124 at grooves 123 (shown it FIG. 3), e.g. it can be frictionally held therein in a slightly compressed state. The fork 124 includes a pair of spaced apart arms 128 connected by a central web 130, which itself is connected to the distal end of the stem 126.

The clamp 104 carried, as above, by the fork 124 of the installation tool 120 can be brought around the lateral masses $M_U$ and $M_L$, and this operation is assisted by the shape of the stem 126 of the installation tool 120 and, more particularly, by the gooseneck-shaped bend 132 thereof. The holding fork arm 128 defines a longitudinal bore 129. The bore is first used as a guide in the drilling of the bone, and is thereafter used to guide the screw 104 into engagement in the bone (lateral masses $M_U$ and $M_L$) and to the clamp 102 from the proximal/posterior opening 108 to the distal/anterior opening 110 thereof. Therefore, the clamp 102 (which may have been custom-produced to comply with the anatomical configuration of the lateral masses $M_U$ and $M_L$ that are intended to be joined thereby) can be brought by the installation tool 120, from a posterior approach, around the lateral masses $M_U$ and $M_L$. Once the clamp 102 has been properly positioned on the lateral masses $M_U$ and $M_L$, it remains held in place by the installation tool 120 while a drill bit if engaged in the bore of the installation tool 120 so that a hole is drilled inter-articularly through the lateral masses $M_U$ and $M_L$ with the drill bit extending through the proximal/posterior and distal/anterior openings 108 and 110 of the clamp 102. The drill bit is then removed from the installation tool 120, and the screw 104 is then introduced in the installation tool's bore, through the proximal/posterior opening 108, obliquely through the bone of both lateral masses $M_U$ and $M_L$, and though (or at least into, e.g. without extending past the clamp 102) the distal/anterior opening 110 of the clamp 102.

Once all of the implants/anchoring devices 100 have been mounted to the concerned vertebrae, osteosynthesis rods are used to connect in a conventional manner the implants/anchoring devices 100 together, at the heads of the polyaxial screws 104. The implant/anchoring device 100 is advantageously independently installed, whereas in conventional plate-based implants, the screw positions are dictated by the fixed plate entry holes. Also, the resulting connection of each clamp 102 with its screw 104 is rigid, which is not the case of the screws used with conventional plates. Optionally a connecting rod may be used to connecting multiple fasteners together. Furthermore, the connection between the implants/anchoring devices 100 and any osteosynthesis rods leaves space so that graft bone can be packed thereat, as opposed to conventional plate-based implants which leave no space to pack graft bone under the screw-plate connection. Moreover, the clamps 102 can be compressed or distracted, which cannot be achieved with successive screws in the conventional plate-based implants. Also, there is no need to remove the clamps 102 in case of revision, whereas in conventional plate-based implants, the screws thereof must be removed in case of revision.

In accordance with another highly advantageous feature, there is provided a method for joining a pair of adjacent upper and lower vertebrae together at the lateral masses thereof. As a preliminary step in the insertion of the device, before surgically installing the screws to hold the vertebrae together, a midline posterior cervical exposure is performed to reveal the lateral aspects of the cervical vertebrae facets. The exposure is extended for one to two levels below an inferior end of the planned arthrodesis to allow for optimal screw placement. In patients with marked degenerative changes, the osteophytes on the dorsal facets are removed to provide better visualization, to help define the anatomy of the facets, and to provide a suitable surface to allow polyaxial screw heads to rotate. However, care should be taken to preserve, where possible, the posterior cortex of the articular mass in order to provide for better screw purchase.

After the incision is made, the method of joining adjacent vertebrae together comprises the steps of: a) providing a clamp and a threaded fastener, the clamp having opposite proximal and distal ends; b) positioning the clamp on an installation tool; c) using the installation tool to position the clamp around the adjacent lateral masses of a pair of vertebra; and d) introducing the fastener through the proximal end of the clamp, through the bone of the lateral mass of the upper vertebra, then through the bone of the lateral mass of the lower vertebra, and into the distal end of the clamp. The fastener engages the proximal and distal ends of the clamp so as to mount the clamp on the lateral masses and join the lateral masses together.

From the foregoing disclosure and detailed description of certain preferred embodiments, it will be apparent that various modifications, additions and other alternative embodiments are possible without departing from the true scope and spirit of the invention. The embodiments discussed were chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An anchoring device adapted to attach an upper vertebra adjacent to a lower vertebra, the anchoring device comprising: a clamp and a fastener;
    the clamp comprising:
        an anterior end block, having a threaded pocket extending only partially through the anterior end block,
        a posterior end block, opposite the anterior end block, having an unthreaded through-hole, and
        a curved medial portion,
        wherein the curved medial portion rigidly connects the anterior end block to the posterior end block,
        wherein the curved medial portion spaces the anterior end block from the posterior end block;
    the fastener comprising:
    a shaft,
    a tip at one end of the shaft,
    a receiving head opposite the tip,
    wherein the receiving head is adapted to receive both an osteosynthesis rod and a securing nut;
    wherein in the installed position:
        the shaft extends through the unthreaded through-hole of the posterior end block,
        the shaft extends through the upper vertebra and the lower vertebra,
        at least a portion of the shaft threadedly engages the threaded pocket of the anterior end block,
        the receiving head is adjacent to the posterior end block, and the anterior end block and the posterior end block remain spaced by the curved medial portion sufficiently to allow the clamp to be positioned around an upper lateral mass of the lower vertebra and a lower lateral mass of the upper vertebra, thereby attaching the upper vertebra to the lower vertebra.

2. A system comprising
the anchoring device of claim 1 and
an installation tool for anchoring the anchoring device, the installation tool comprising
a handle and
a clamp-holding head adapted to retain the clamp until the clamp has been secured to the lateral masses by the fastener.

3. The system of claim 2 wherein the installation tool further comprises a bend between the handle and the clamp-holding head, wherein the bend provides clearance around the vertebra allowing the head to hold the clamp in the installed position.

4. The system of claim 2 wherein the installation tool defines a bore aligned with the openings defined at the opposite ends of the clamp, wherein the bore allows the fastener to be inserted therein.

5. The system of claim 2, wherein the clamp defines a pair of grooves adapted to receive the alignment tool, wherein the grooves are positioned generally adjacent a pair of ends of the clamp.

6. The anchoring device of claim 1, wherein the threaded opening is formed as a pocket at the anterior end of the clamp.

7. The anchoring device of claim 1 wherein the fastener extends trans-articularly between adjacent vertebra.

8. The anchoring device of claim 1 wherein the fastener is a polyaxial screw.

9. The anchoring device of claim 1 further comprising multiple fasteners and a rod connecting the multiple fasteners together.

10. The anchoring device of claim 1 wherein the adjacent vertebra form a spinal column, the fastener is a screw having a head and an end opposite the head, and in the installed position the end of the screw extends in a downward direction such that the head of the screw extends from the upper vertebra and the screw end extends from the lower vertebra.

* * * * *